United States Patent [19]

Tompa et al.

[11] Patent Number: 4,671,870
[45] Date of Patent: Jun. 9, 1987

[54] APPARATUS FOR OVERPRESSURED THIN-LAYER CHROMATOGRAPHIC TECHNIQUE

[76] Inventors: Ildikó F. Tompa, Szamóca ut 2., 2013 Pomáz; Attila Nagy, Füredi ut 15., 1144 Budapest; Ernö Tyihák, Zápor u. 59., 1032 Budapest; Szabolcs Nyiredy, Moszkva tér 8., 1024 Budapest; Gizella V. Petri, Üllöiloi ut 44., 1082 Budapest; Sándor Mészáros, Fogarasi ut 74/B, 1148 Budapest; László Szepesy, Zenta u. 5., 1111 Budapest; László Vida, Árpád fejedelem ut 22., 1023 Budapest; Emil Mincsovics, Vásárhelyi K.tér 4., 2000 Szentendre; Gábor Kemény, Érdi ut 10/a, 1112 Budapest; Piroska Baranyi, Ond vezér ut 10., 1144 Budapest, all of Hungary

[21] Appl. No.: 724,524

[22] Filed: Apr. 18, 1985

[51] Int. Cl.⁴ .............................................. D01A 15/08
[52] U.S. Cl. .................................... 210/149; 210/658; 210/198.3
[58] Field of Search ...................... 210/658, 149, 198.3

[56] References Cited

U.S. PATENT DOCUMENTS 3,864,250  2/1975  Perry .................................. 210/198.3
4,346,001  8/1982  Tyihak .............................. 210/198.3
4,469,601  9/1984  Beaver et al. ..................... 210/198.3

FOREIGN PATENT DOCUMENTS 1132224  10/1984  U.S.S.R. ........................... 210/198.3

OTHER PUBLICATIONS

Microcomputers in Chemical Engineering R&D by Patterson, Chemical Engineering Progress, pp. 63–68, Nov. 1981.

Primary Examiner—John Adee
Attorney, Agent, or Firm—Michael N. Meller

[57] ABSTRACT

The invention relates to an apparatus for overpressured thin-layer chromatographic technique, comprising at least one carrier plate arranged adjacent a closed space, a sorbent layer arranged on the surface of said carrier plate, means for covering the surface of said sorbent layer under influence of overpressure generated in said closed space, a first inlet for admitting solvent to said sorbent layer, a second inlet for admitting overpressurizing medium into said closed space, a heating unit for altering temperature of said sorbent layer and a temperature control unit for energizing said heating unit. The apparatus according to the invention ensures improved efficiency of the chromatographic developments carried out under overpressure. By means of the apparatus chromatograms can be obtained with increasing speed of separation.

20 Claims, 14 Drawing Figures

APPARATUS FOR OVERPRESSURED THIN-LAYER CHROMATOGRAPHIC TECHNIQUE

BACKGROUND OF THE INVENTION

The present invention relates to an apparatus for carrying out chromatographic separations by means of the overpressured thin-layer chromatography. According to art the known apparata include a carrier plate covered by a sorbent layer receiving the samples to be investigated and elements defining a closed space wherein overpressure can be generated for pressing a flexible element to the sorbent layer or the sorbent layer to an appropriate element. The efficiency of the separation technique realised by means of overpressure thin-layer chromatography can be improved when applying the invented apparatus.

The advantages offered by the column chromatography and its planar version, the so called thin-layer chromatography, can be effectively combined by the method of overpressured thin-layer chromatography presented e.g. in GB-PS 1 570 760. According to the specification of this patent an apparatus for realizing the method includes an overpressured chamber adjacent to a sorbent layer. As sorbent the same organic and inorganic materials can be applied as in both parent methods. The sorbent layer is covered completely by a plastic plate made advantageously of flexible material which is pressed to the layer by means of overpressure generated in the closed space, e.g. by water supplied therein. Means are applied for blocking the solvent from leaving the sorbent layer, e.g. by a sealing layer around this layer to be connected with the plastic plate. This results in virtual elimination of the vapor space which is characteristic for the known thin-layer chromatography. The vapor phase realized over the sorbent layer is deemed to be the source of some disadvantages. The plate carrying the sorbent layer should be, as mentioned, sealed on the edges in order to prevent leaking of the eluant (solvent) admitted to the sorbent layer under the influence of overpressure transmitted by the plastic plate. The migration of the eluant can be prevented by means of channels formed in the sorbent layer or by a plastic plate pressed onto the surface of this layer.

For improving the efficiency of the known overpressured thin-layer chromatographic techniques a higher number of sorbent layers can be arranged in a chamber. In this case the carrier plates are stacked above one another and form a parallel system wherein the sorbent layers lie on the same side of these plates. An apparatus of this kind is shown e.g. in Hungarian Patent Application 1335/82, the early publication of which took place in February 1985. The carrier plates should be sealed to one another on their edges by applying an appropriate sealing medium. The overpressured closed space can be realized either over the upper or under the lower carrier plate and in this case the carrier plates transmit the overpressure in the system. Usually the carrier plates are equipped with a system of parallel channels beginning from one of the edges or from the middle of the sorbent layer, wherein the eluant can communicate between the sorbent layers.

The chromatographic separation cannot be carried out with high efficiency unless the basic conditions of separation are selected in an appropriate way. The basic conditions of liquid chromatography are: the material of the sorbent, the mobile phase—eluant, the temperature of the separation, etc. The temperature is an important parameter in the gas chromatography techniques and it is selected therein very carefully. The desired temperature value is maintained during the separation with high accuracy. To date the skilled artisans have believed that the role of temperature is not important in liquid chromatography, as it follows clearly from the practice of carrying out column chromatographic techniques.

The known apparata of thin-layer chromatography work practically with taking into account thermal effects. For example, in the book of J. C. Touchstone and M. F. Dobbins, "Practice of Thin-Layer Chromatography", edited by J. Wiley, New-York, 1978 it is stated on p. 304 that the role of temperature is unimportant in this technique. The statement follows obviously from the fact that a vapor space is present over the sorbent layer in the known apparata and this space has a disadvantageous influence on the conditions of the separation at increased temperatures. For detecting small amounts of different materials it has been proposed to use increased temperature around the chamber during separation and this proposal relates to the method of multiple development wherein the increased temperature is applied for vaporization of the solvent used in the previous development which should be expelled. In a single development the increased temperature and the thereby accelerated vaporization of the solvent can cause many problems because of the closed vapor space over the sorbent layer and therefore the separations are often evaluated with low efficiency and reliability. The vapor of the solvent is a source of inaccuracy.

Of course, the sorbent layer can be placed together with the chamber in an incubator ensuring a stable temperature value selected according to the materials to be separated. This is a known feature of the thin-layer chromatographic developments.

In comparison to the traditional gas chromatographic techniques, the classical liquid column chromatography offers, owing to the large sorbent particles applied, decreased speed and efficiency. The liquid column chromatography was developed because the gas chromatography is applicable only to about 20% of all organic substances. The planar methods, and especially the thin-layer chromatography techniques, proved very useful in the view of the following advantages: they are simple and highly economical in time and materials, and offer the possibility of visual detection and simultaneous study of a large number of samples wherein aggressive reagents may be applied, too. Some drawbacks should be mentioned also. These are the limitation of the number of separations by the length of the carrier plate and the long time required for development. The overpressured thin-layer chromatography methods ensure rapid and effective separation of mixtures of various organic and inorganic substances which are effected about 5 to 20 times faster than by the traditional thin-layer methods, however, they require applying smaller and more uniform sorbent particles than was previously the case.

The efficiency of the separation and its rapidity are in many cases not satisfactory, especially in the case of mixtures comprising a large number of organic compounds, wherein the separation is weak. It is difficult to separate the materials and evaluate the chromatograms obtained.

The problem of the invention is to elaborate a method and an apparatus for improving the efficiency and rapidity of the separations carried out by means of the overpressured thin-layer chromatographic methods.

The invention is based on the recognition that the overpressured thin-layer chromatography can be improved in spectacular manner when applying a temperature program during development. The temperature is a very important parameter—in spite of the beliefs holding sway to date in the field of thin-layer chromatograhy—when the vapor phase can be eliminated, i.e. in the methods of the overpressured thin-layer chromatography. It is important also that the eluant flows under the influence of the overpressure in predetermined directions and that the speed of this flow can be altered by the temperature, too. According to the foregoing recognition the basic feature of the invention lies not in the application of the temperature itself, but in the changes thereof. Thereby it is possible to cause changes in the sequence (in the spatial arrangement, of the materials separated in the sorbent layer. This improves the separations of the different components of the mixture in comparison to the known methods. The higher speed of separation ensured by the increased temperature makes it possible to use also on-line methods of evaluation. The invention is based further on the fact that the increased temperature causes the material pressed to the sorbent layer to absorb the eluant on another condition than in the case of lower temperature and therefore a very limited space of special vapor pressure is realized over the sorbent layer, influencing the separation, the order (sequence) of the components and especially the efficiency in advantageous manner.

SUMMARY OF THE INVENTION

For solving the problem set forth above, the object of the invention is an apparatus realizing an improved method of overpressured thin-layer chromatography wherein in comparison to the known methods of this chromatographic technique a temperature program is applied and the temperature can be changed in a timely determined sequence in a different way at different points of the space including a sorbent layer with materials to be separated.

Hence, the object of the invention is an apparatus comprising at least one carrier plate arranged adjacent a closed space, a sorbent layer arranged on the surface of the carrier plate, means for covering the surface of the sorbent layer under the influence of overpressure generated in the closed space, e.g., a flexible plate, a first inlet for admitting solvent to the sorbent layer, a second inlet for admitting overpressurizing medium into the closed space, a heating unit for altering the temperature of the sorbent layer and a temperature control unit for energizing the heating unit according to a predetermined time and/or space function.

The heating unit includes preferably a carrier plate capable of receiving electromagnetic energy from an induction heating unit or heating elements which are plate shaped and are arranged parallel to the carrier plates. The number of heating elements and carrier plates can be higher than one, and it is advantageous to arrange them in a parallel system. The carrier plate can be in contact with heat insulation elements also.

According to the invention the apparatus includes preferably a central microprocessor unit controlling the temperature of the carrier plates and heating elements whereby the temperature distribution in the solvent layer can be altered in a time and spatial sequence, according to a program stored in the central microprocessor unit.

In a further advantageous embodiment of the apparatus according to the invention the temperature control unit includes a temperature sensor for detecting temperature of the sorbent layer, connected via a differential amplifier to an input of a compartor, over first input of a comparison amplifier, wherein a second input of the comparison amplifier is connected to an output of a series member including a control keyboard for programming the central microprocessor unit and an integrator, said comparison amplifier forwarding signals of high positive level $U_c$ if signal level $U_a$ on its first input is higher than the level $U_b$ on its second output, signals of low positive level $U_c$ when signal level $U_a$ on its first input is approximately the same as the level $U_b$ of the signal on its second input, and signals of negative level $U_c$ when the signal level $U_a$ on its first input is lower than the level $U_b$ of the signal on its second input, another input of the comparator being connected via a level shifting unit to an output of a relaxation oscillator, and the output of the comparator being coupled with a power switch, the output of which forms a control output of the temperature control unit.

The apparatus as proposed by the invention applies temperature changes to sorbent layers for improving thereby the separation of different components of a mixture comprising organic and inorganic compounds. The improved efficiency of the separation increases the reliability of evaluation of chromatograms made on the basis of the method of overpressured thin-layer chromatography.

BRIEF DESCRIPTION OF THE DRAWINGS

The invention will be better understood when considered together with the attached drawings showing by way of examples some preferred embodiments of the apparatus proposed. In the drawing

DESCRIPTION OF THE PREFERRED EMBODIMENTS

Figure 1:
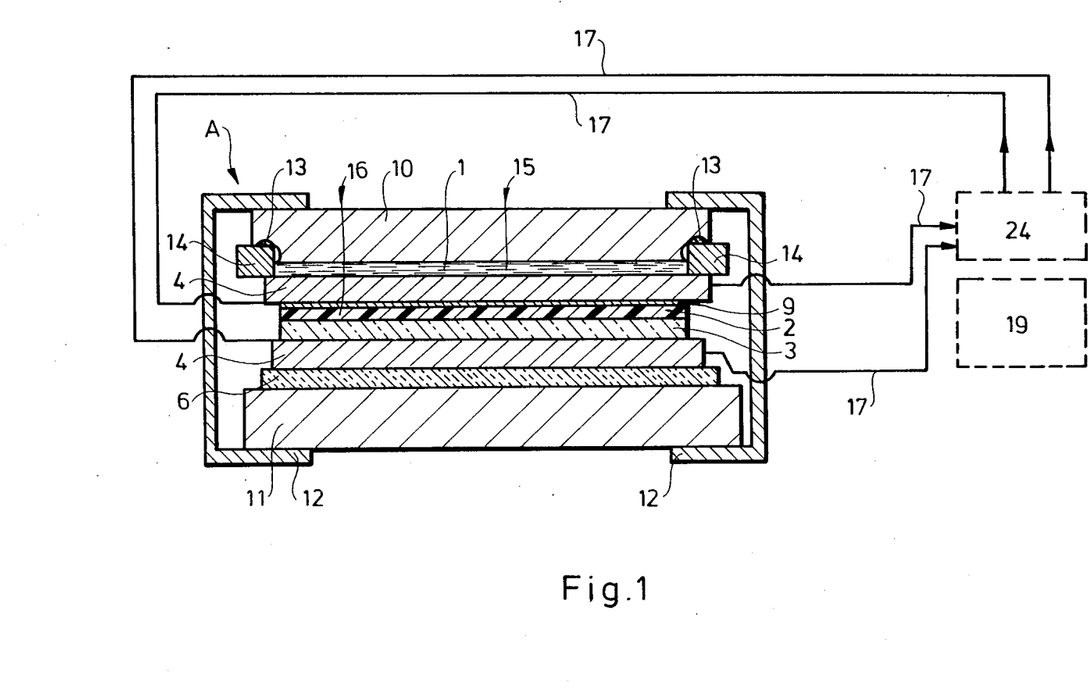
FIG. 1 is a cross-sectional view of a preferred embodiment of the apparatus according to the invention when applying one carrier plate.

According to the invention an apparatus A has been developed (FIG. 1) which includes one or more carrier plates 3 arranged in a clamp 12 or other appropriate element capable of rigidly supporting the elements of the apparatus. The carrier plate 3 is covered at least on one side by a sorbent layer 2 and is in thermal contact with a heating unit capable of changing the temperature of the sorbent layer 2 in time and if necessary in spatial sequence. In the apparatus A, as shown in FIG. 1, the heating unit includes two plate-shaped heating elements 4 supplied with electric current. One of the heating elements 4 is arranged over the sorbent layer 2 separated therefrom by an insertion plate 9 made of flexible material. The other heating element 4 is placed below the carrier plate 3. The heating elements 4 are advantageously parallel to the carrier plate 3 and they are obviously of controlled power. If a spatial temperature sequence is desired, the heating elements can be divided into independent parts each connected to a controlled power supply. The lower heating element is supported by a plate 11 fitted in the clamp 12 wherein a heat insulation layer 6 can be applied between the plate 11 and the heating element 4. A first inlet 16 communicates with the sorbent layer 2 for admitting solvent (eluant) to appropriate points thereof. Over the upper heating element 4 there is a closed space 1 limited laterally by a closing plate 14 and in the axial direction by a plate 10 wherein an O-ring 13 is applied between plates 10 and 14 for sealing. The closed space 1 is capable of maintaining an overpressure generated therein by admitting an appropriate overpressurizing medium, such as water or gas, by way of a second inlet 15. Under the influence of the overpressure generated in the closed space 1 advantageously by means of a liquid pocket, the upper heating element 4 is pressed against the sorbent layer 2 by way of the insertion plate 9. The heating elements 4 are connected by means of conductors 17 to respective inputs and outputs of a temperature control unit 24. The heating elements 4, which, as mentioned, can be divided into more parts, and temperature sensing means coupled therewith or with the respective areas of the sorbent layer 2 are connected each to separate inputs and outputs of the temperature control unit 24. The parts of the heating elements 4 are advantageously elements of controlled power and this is the basis of changing the temperature in the environment of the sorbent layer 2 according to a predetermined time and spatial program. This program is disclosed in the appendix. Under the influence of the solvent introduced by way of the first inlet 16, samples brought onto the surface of the sorbent layer 2 will be separated and the separation can be evaluated by means of a detector 19. In the case of on-line evaluation, the detector 19 includes detecting means arranged at one of the edges of the carrier plate 3. When evaluation takes place by the off-line method, then the detector 19 is fully independent of the apparatus A, and the carrier plate 3 should be removed from the apparatus A for evaluation.

The temperature control unit 24 realizes the temperature control usually by regulating the power consumed by the parts of the heating unit.

Figure 2:
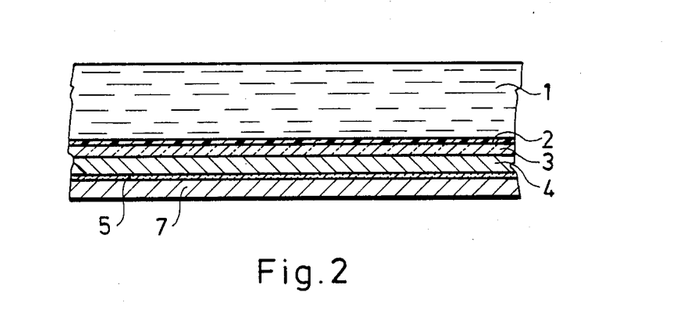
FIG. 2 is a cross-sectional view of the arrangement of the carrier plate with a sorbent layer and a heating element.
Figure 3:
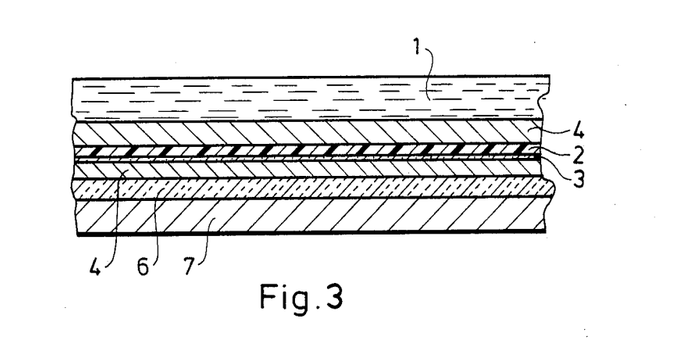
FIG. 3 is a cross-sectional view of a proposed arrangement of the carrier plate with the sorbent layer between two heating elements.

The sorbent layer 2, the carrier plate 3 and the heating element 4 can be arranged in many possible ways. One of the possibilities is to arrange the heating element 4 on a base plate 7 (this can be e.g. the plate 11) over a heat insulation layer 5. The heating element 4 is covered by the carrier plate 3 with the sorbent layer 2 on its opposite surface. An appropriate flexible plate lying on the sorbent layer 2 transmits the overpressure from the closed space 1 (FIG. 2). As shown in FIG. 3, two heating elements 4 and the carrier plate 3 can form a sandwich structure, wherein the closed space 1 can be arranged on one side of one of the heating elements 4, i.e. over the upper or below the lower heating element 4; the other heating element is supported by the heat insulation plate 6 clamped by appropriate elements together with the base plate 7.

Figure 4:
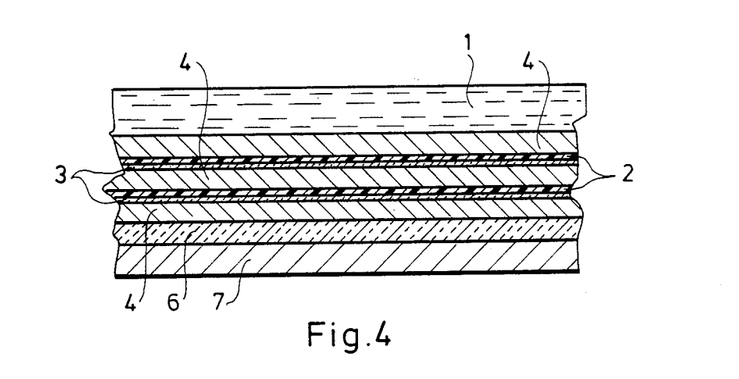
FIG. 4 is a cross-sectional view of the arrangement with the sorbent layers on respective carrier plates and two heating elements.

The apparatus as proposed by the invention can be used advantageously with a greater number of carrier plates 3. One possibility is, as shown in FIG. 4, that the carrier plates 3 are arranged with sorbent layers 2 facing the same direction and with heating elements 4 above, below and between the carrier plates. One heating element 4 transmits in this case also the overpressure from the closed space 1 and another heating element 4 is supported by a heat insulation plate 6 arranged on the base plate 7.

Figure 5:
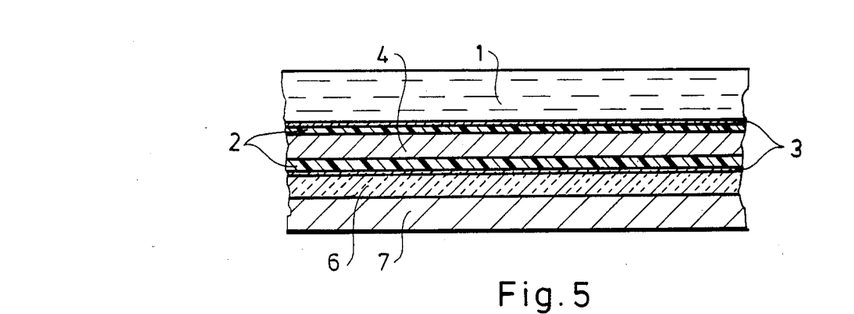
FIG. 5 is a cross-sectional view of an arrangement with two carrier plates and a heating element therebetween for heating two sorbent layers.

A further possibility of an arrangement comprising two carrier plates 3 is shown in FIG. 5, wherein a heating element 4 is arranged between the carrier plates 3, i.e. the heating element 4 is separated from the sorbent layers 2 by the carrier plates 3, or the sorbent layers 2 face the heating element 4. In this last case the structure comprising the sorbent layers 2 is closed by the carrier plates 3. The closed space 1 generates overpressure from one side of the heating element 4 and a heat insulation plate 6 gives it support on a base plate 7.

Figure 6:
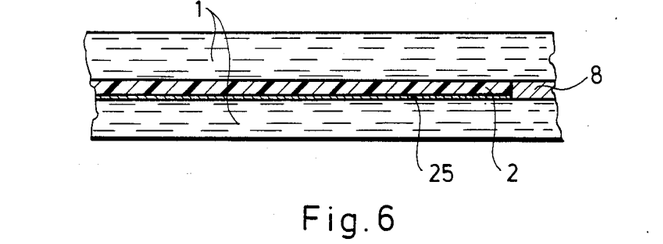
FIG. 6 is a cross-sectional view of an arrangement with an inductively heated carrier plate arranged between two closed spaces.

The heating unit of the apparatus A can cooperate with a system of induction heating. In this case the temperature control unit 24 energizes an induction heating unit coupled with a carrier plate 25 made of metal (FIG. 6) and supported by a supporting plate 8. Under the influence of the induction heating, the carrier plate 25 and thereby the sorbent layer 2 covering it are heated up on at least one side.

The carrier plates 3 and 25 can consist of, as previously mentioned, more than one part. The material thereof can be glass, ceramics, aluminum or therephthalate-based polymer. The closed space is arranged on at least one side of the heating unit. The carrier plate 3 is square or rectangular, however, other shapes can be used, too. For on-line evaluation it is preferred to give carrier plate 3 at least one straight edge. The usual carrier plate 3 is as thick as 0.1 to 5.0 mm. The higher thickness values ensure higher rigidity of the carrier plate at the expense of higher power expenditures for temperature conditioning of the carrier plate. The selection depends on the given conditions and is a routine object for a skilled artisan.

In the apparatus proposed by the invention the closed space 1 with overpressure generally comprises a water pocket, because for safety reasons this seems to be the best solution. On the other hand, pressurized air can ensure the same effect. The carrier plates 3 should be rigidly supported against the overpressure by means of the base plate 7, plates 10, 11 and clamps 12.

The sorbent layer 2 can consist of organic and inorganic materials. As examples silica-gel, aluminum oxide and cellulose or synthetic resins can be mentioned. These examples, obviously, do not exhaust all possibilities.

The material pressed to the sorbent layer 2 of the carrier plate 3 for transmitting overpressure, e.g. the insertion plate 9, usually consists of polytetrafluoroethylene, terephthalate based polymer, polyethylene, or aluminum foil. This material should be selected according to the conditions of the chromatographic separation. The aluminum foil can separate the sorbent layer 2 from the closed space 1 as an elastic layer.

The parts of the apparatus A serving as heat insulation consist generally of asbestos, however, it is obvious to use other appropriate materials.

The examples of different materials to be used when preparing the apparatus A according to the invention present only some preferred possibilities and it should be understood that a skilled artisan can select other appropriate materials, too, on the basis of the known conditions of a chromatographic development.

Figure 7:
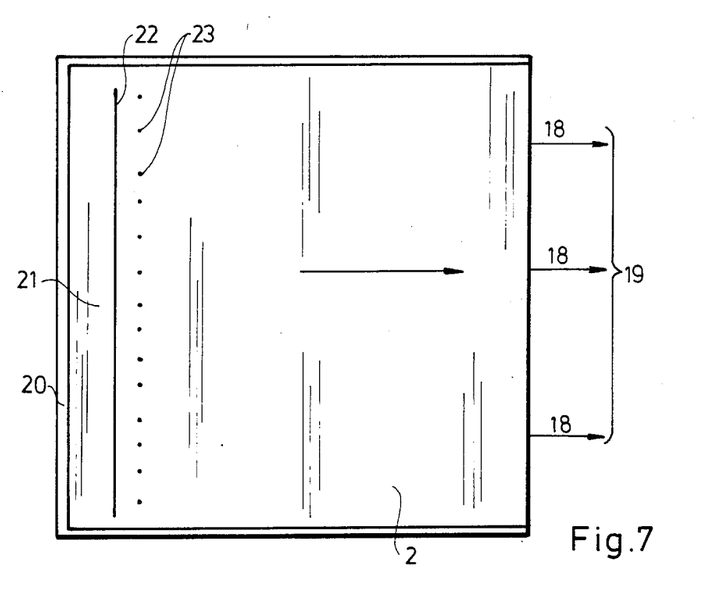
FIG. 7 is a top view of a carrier plate for linear development used in on-line evaluations.
Figure 8:
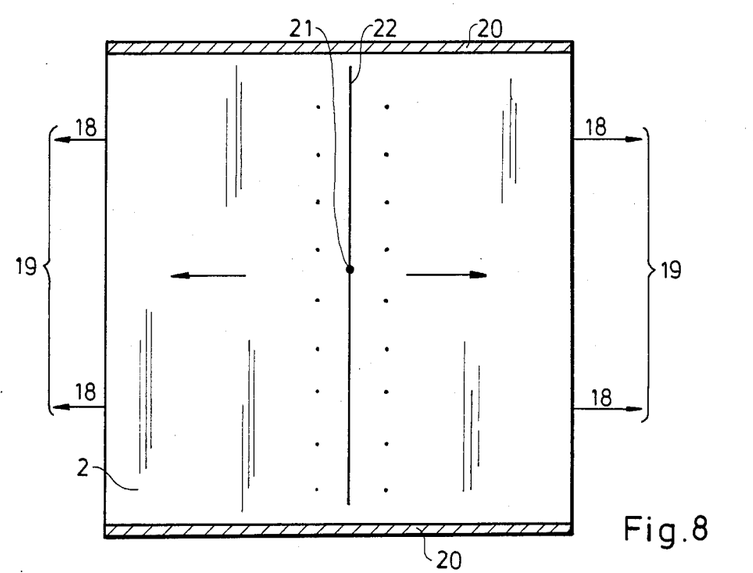
FIG. 8 is a top view of a carrier plate for two-directional developments used in on-line evaluations.
Figure 9:
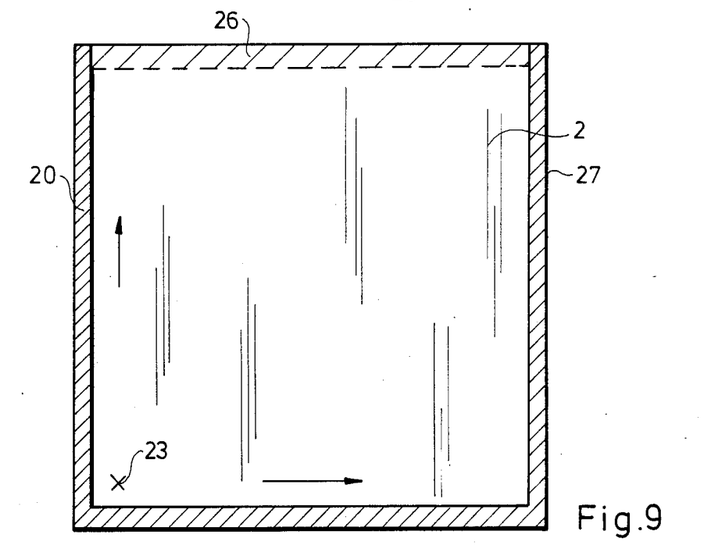
FIG. 9 is a top view of a carrier plate for two-directional developments used in off-line evaluations.
Figure 10:
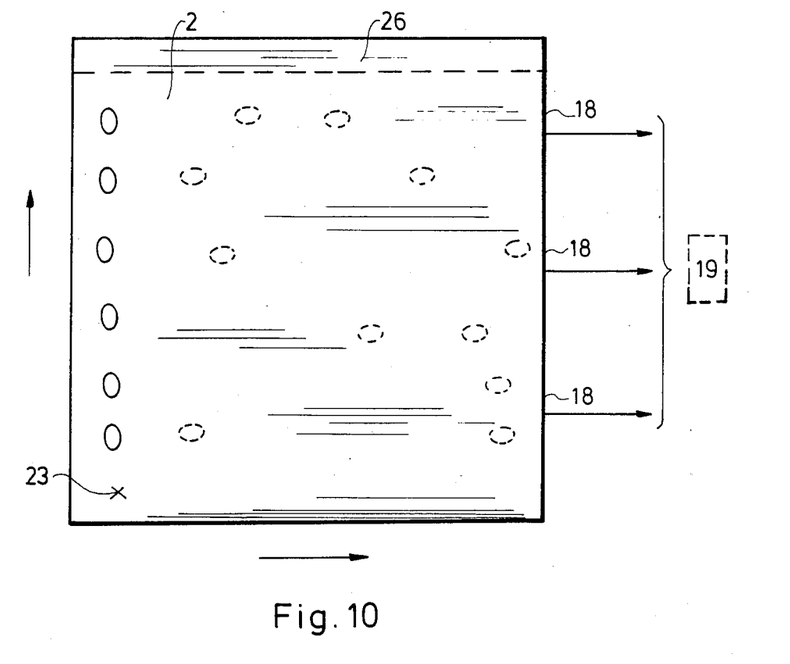
FIG. 10 is a top view of a carrier plate for two-dimensional developments used in on-line evaluations.

In the apparatus according to the invention it is obviously preferred to use rectangular carrier plates 3, whereon the sorbent layer 2 is bordered (FIGS. 7-10) by a sealing layer 20 on three sides. On the sorbent layer 2 there are inlet points 21 and charging points 23. These points 21, 23 are situated according to the conditions of the development. They can be selected on one edge of the sorbent layer 2, opposite to a free edge 18 carrying no sealing layer 20 or in the middle part thereof. Of course, other possibilities can be realized, too. The inlet points 21 receive the eluant and the charging points 23 (starting points) cumulate the samples. The overpressure makes the eluant flow over channels 22 on the sorbent layer 2 wherein the eluant can move in these channels, as shown by arrows in FIGS. 7 and 8, in the direction of the edge 18 of the carrier plate 3. During this movement the separation of the sample takes place into components. In the case of on-line development the eluant should reach the edge 18 together with the component and then it can be detected by means of appropriate arrangements, as for example by an optoelectronic detecting unit. The detection is the basis for generating signals transmitted to the detector 19. As shown in FIGS. 7 and 8, the carrier plates 3 can be used for one-dimensional developments evaluated by the on-line method. If the evaluation is carried out by off-line methods, then the components separated on the sorbent layer 2 travel different distances the length of which depends on the given component separated and the conditions of developments. The distance between the charging points 23 and the spot of the component is the basis of evaluation. The separation can be carried out by a two-dimensional method, too. In this case the separation takes place at first in the direction of a closing strip 26 and in the second step in the direction of another closing strip 27 lying perpendicular to the first strip (FIG. 9, off-line evaluation). The two directions of the development can be determined also by the edge 18 of the carrier plate 3, and by the closing strip 26 with empty parts prepared by cutting out some parts of the sealing layer 20 (FIG. 10, on-line evaluation). During two-dimensional development a first solvent is to be used, the residue of which can be removed by an appropriate inert gas, and then a second solvent ensures the separation in the other direction. Because of the absence of a greater vapor space over the carrier plate 3 it is not necessary to take into account the harmful influence of the solvents on the next development. During development the temperature of the sorbent layer 2 can be altered according to a predetermined program.

Figure 11:
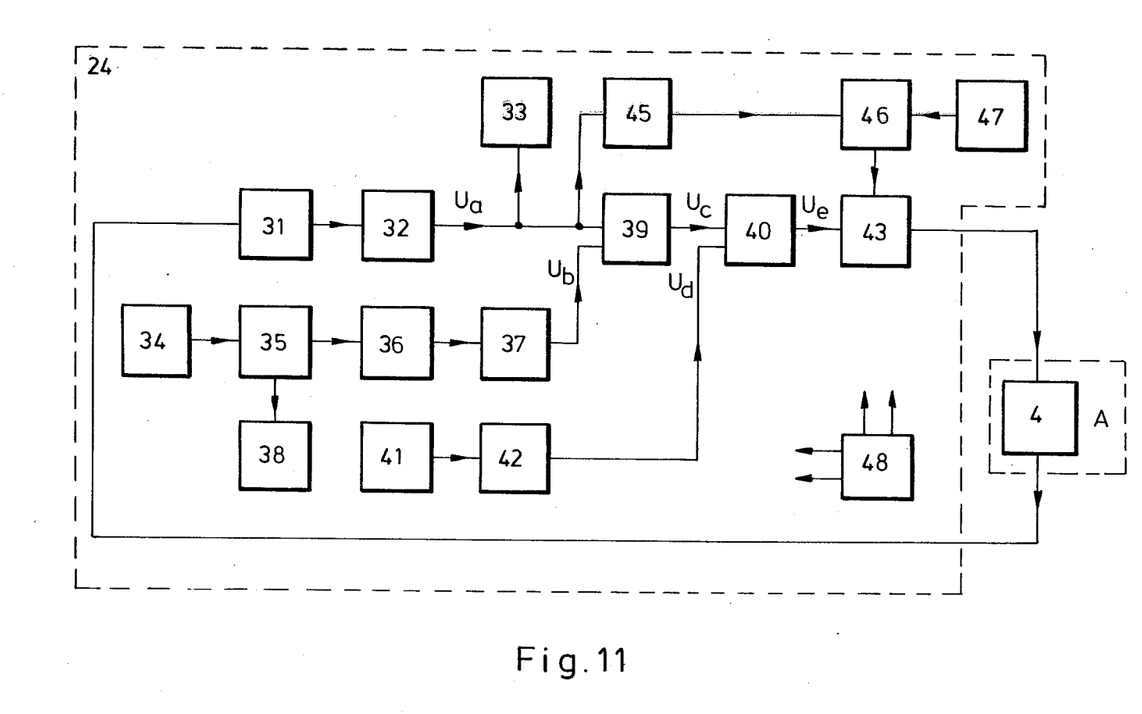
FIG. 11 is a block diagram of a preferred embodiment of the temperature control unit used in the apparatus according to the invention.
Figure 12:
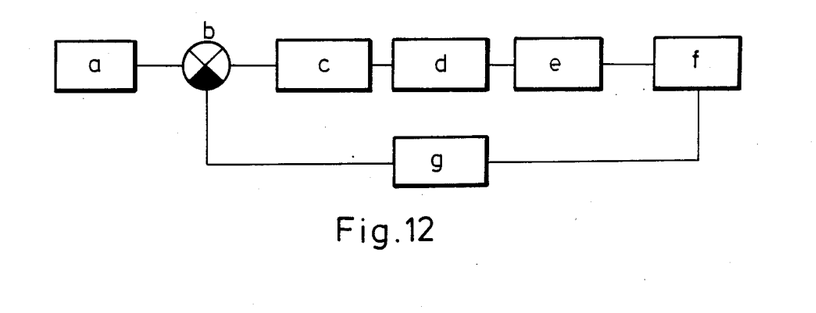
FIG. 12 is a block diagram of the temperature control applied in the apparatus.

The temperature control unit 24 (FIG. 11) is coupled with the heating element 4 or metallic carrier plate 25 of the apparatus A, and the coupling element is a temperature sensor 31 or a system of temperature sensors 31, arranged for detecting the temperature of different parts of the sorbent layer 2. The temperature control unit 24 regulates the power of the heating elements 4 or the quantity of electromagnetic energy forwarded to the metallic carrier plate 25 and the cooperation of the two units ensures a feedback circuit according to FIG. 12, wherein a unit a for providing a reference signal (i.e. the unit for programming the changes in temperature) is connected to a comparator b. Comparator b is connected to an amplifier c, and a signl forming unit d is connected to the output of the amplifier c. Unit d comprises a thyristor or other appropriate element for regulating output power. The signal forming unit d sends the signal to an intervention unit e and thereby to means f for ensuring the regulation of the temperature in the apparatus according to the requirements. The last unit is connected through a feed-back network g to the comparator b, which generates signals which correspond to the difference of the input signals. The comparator b can be realized e.g. on the basis of platinum thermoelements. A preferred embodiment of the feedback system shown in FIG. 12 is the temperature control unit 24 of FIG. 11.

The temperature of the sorbent layers 2 is detected during the chromatographic developments at one or more points, as previously mentioned, by means of temperature sensors 31.

The outputs of the temperature sensors are connected by way of a differential amplifier 32 to a temperature display 33, immediately to a comparator 45 with hysteresis and also immediately to a first input of a comparison amplifier 39. The comparison amplifier 39 is a logic circuit element generating an output signal of $U_c$ level which is of high positive level, low positive level or negative level depending on the level of signals arriving at its inputs. Comparison amplifier 39 has at least a first input receiving signals of $U_a$ level, a second input receiving signals of $U_b$ level and generates signals of $U_c$ level on its output. The level $U_c$ is the high positive level when $U_a$ is greater than $U_b$, is lowered when the difference between the levels $U_a$ and $U_b$ becomes smaller and reaches a relatively low positive level when the two levels are equal or approximately equal. The level $U_c$ is negtive when $U_a$ is less than $U_b$.

The second input of the comparison amplifier 39 is coupled with a series connection including a control keyboard 34 or other input means, a central microprocessor unit 35 connected to a second temperature display 38, an optical switch 36 and an integrator 37, wherein the optical switch 36 is used for coupling the integrator 37 and the central microprocessor unit 35 without an electrical connection. The temperature display 33 shows the temperature values detected in the sorbent layer 2 and the second temperature display 38 shows the values programmed into the central microprocessor unit 35. The control keyboard 34 or other appropriate input means are intended for programming the central microprocessor unit.

The output of the comparison amplifier 39 is connected to an input of a comparator 40 for receiving signals of $U_c$ level, wherein the comparator 40 has a second input receiving signals of $U_d$ level generated by a level shifting unit 42 from the signals of a relaxation oscillator 41, which is preferably a saw-tooth generator. The output of the comparator 40 transmitting signals of $U_e$ level is connected to an input of power switch 43, which generates signals for controlling the heating unit of the apparatus A, e.g. the heating elements 4 coupled with the sorbent layers 2 of chromatographic developments. The comparator 45 with hysteresis is connected to a relay 46 which opens on given conditions the current path from a high-power supply unit 47 to power switch 43. The different units of the temperature control unit 24 requiring supply are connected to supply means 48.

Figure 13:
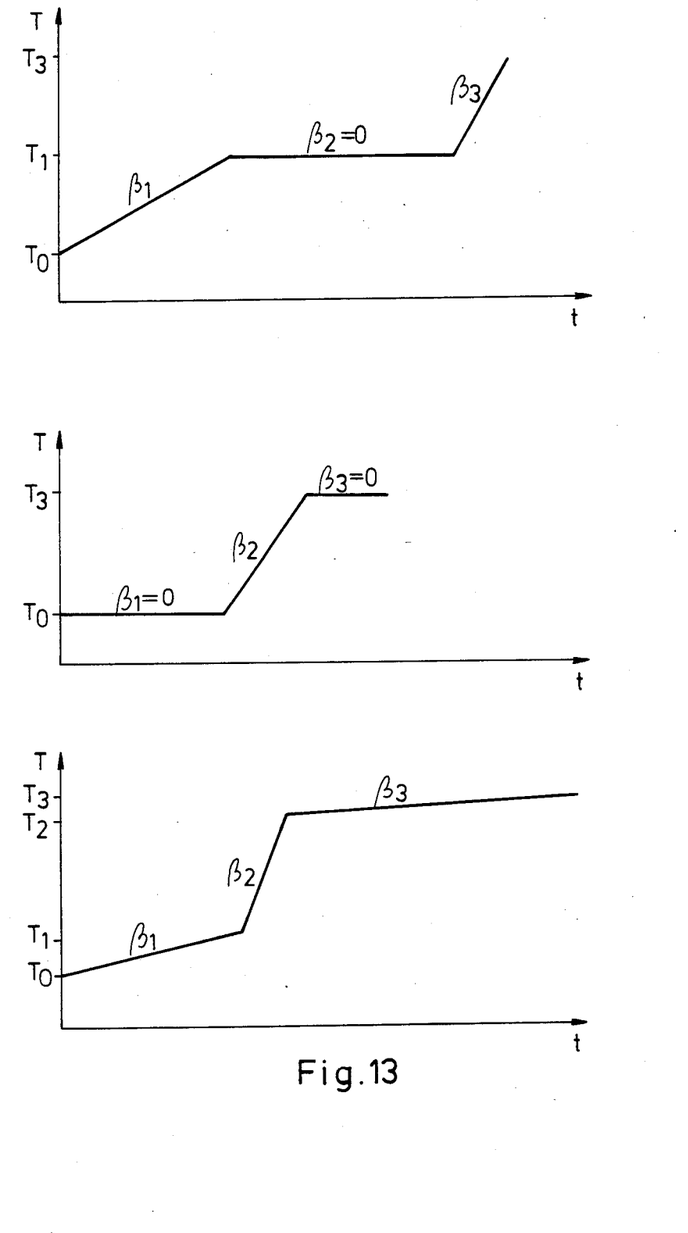
FIG. 13 shows some possibilities of the temperature programming used for controlling the heating unit.

The temperature control unit 24 ensures regulation of the temperature according to a predetermined program which can be put into the apparatus by means of the control keyboard 34 cooperating with the central microprocessor unit 35. The program can realize the alteration of the temperature of the sorbent layers 2 and carrier plates 3 according to FIG. 13. This alteration means the change of the temperature with time t. The basic value of the temperature is $T_0$ and this is to be increased to a top value $T_3$ greater than intermediate values $T_1$ and $T_2$ with respective characteristic slopes $\beta_1$, $\beta_2$ and $\beta_3$. Of course, the programming means renders determination of different temperatures and slopes possible. The lines connecting the mentioned temperature values can be also nonlinear when desired.

During operation of the temperature control unit shown in FIG. 11 it is generally enough to increase temperature at most to 90° C. and the required temperature values should be ensured with an accuracy of ±1° C. The repeatability of the temperature values should be about 0.5° C. During the measurements it is preferred to set the speed of the temperature change in the range from 1° to 20° C./min. When applying the temperature control unit 24, the comparison amplifier 39 generates signals $U_c$ on the basis of the temperature conditions as mentioned above, ensuring the intensity of heating to depend on the difference between the temperatures set and measured, switching the power supply off when the temperature of the carrier plate 3 or the sorbent layer 2 is higher than the predetermined programmed value. The signals with $U_e$ level on the output of the comparator 40 consist of rectangular pulses with width and interval depending on the difference of the temperature values, i.e. on the input signals of the comparator 40. If the temperature of the sorbent layer 2 is higher than the programmed value, then signals are generated whereby the heating is stopped.

The comparator 45 with hysteresis, the relay 46 and the high-power supply unit 47 have protection functions. The comparator 45 with hysteresis generates output signals in the case when the temperature detected in the sorbent layer 2 is higher than the maximal value allowed for the system, e.g. due to an error of the electric circuits. In this case the relay 46 closes the contacts and the current sent by the high-power supply unit 47 ensures the interruption of the current path to the apparatus A and its heating unit.

The temperature sensor 31 preferably consists of a seizing unit and a current generator wherein the sensing element arranged in one branch of the generator is coupled with the carrier plate 3 and the sorbent layer 2. The mechanical connection of these elements is possible, too. The last solution ensures a high level of thermal coupling. The central microprocessor unit can be based on well-known units 8080 or 8085 connected through an optical switch 36 to the integrator 37 because in this case no grounding is required. The power switch 43 is e.g. a transistor unit with a Darlington circuit.

The heating element 4 is preferably a circuit plate with strip-formed paths for dissipating energy. A part of the paths can be used for detecting temperature.

Figure 14:
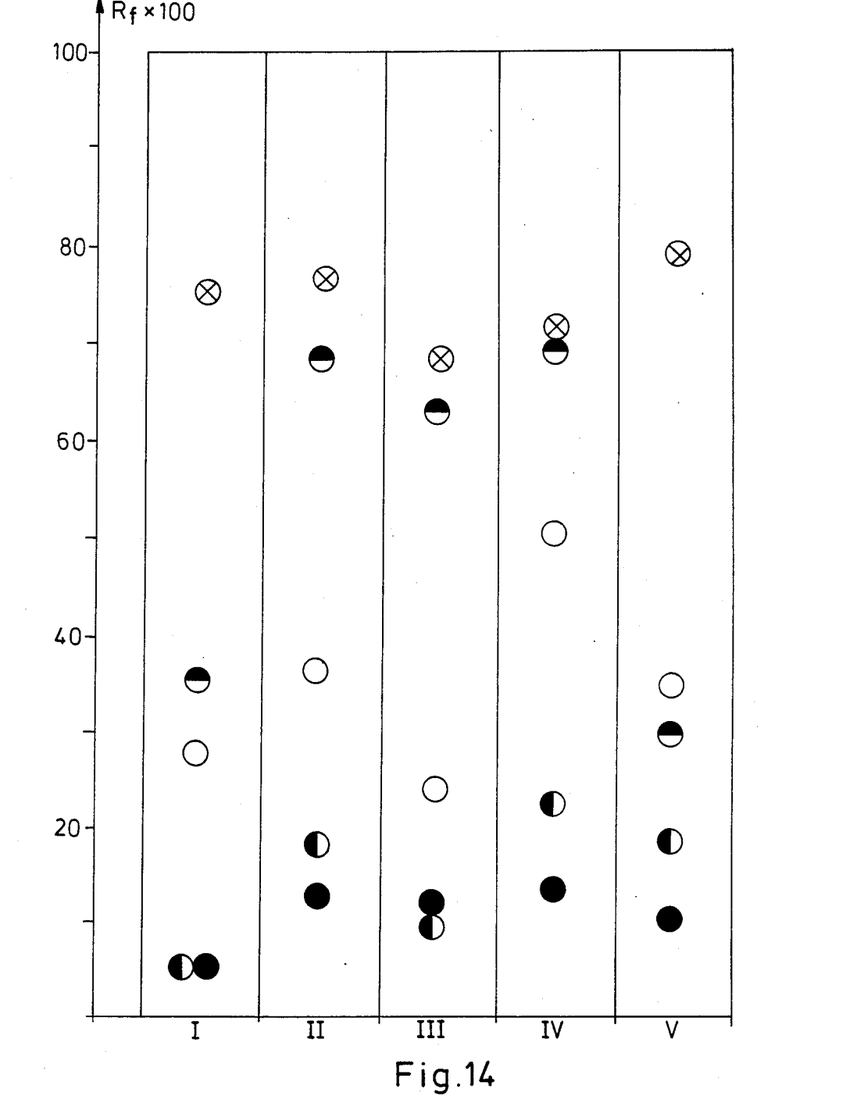
FIG. 14 is a schematic view of separations obtained by applying different values of $100R_f$ ($R_f$ means retarding factor) on samples containing nicotine alkaloids.

During developments to be evaluated by off-line methods the separation schema according to FIG. 14 can be obtained for the nicotine alkaloids, wherein the influence of temperature can be observed. The retarding factor $R_f$ shows increasing values with increasing temperature contrary to the known thin-layer chromatography characterized by undesirble decrease of this value. The nicotine alkaloids can be generally separated into five compounds which, as it can be seen from FIG. 14, travel different distances under the influence of different temperature programs. The temperature programs can be determined selectively. For example, programs II and V ensure a very good evaluatable chromatogram, wherein the separation is very good. When selecting other programs, separations can be obtained wherein some compounds occupy the same place or are very close to one another (programs I, III and V). The optimal program should be determined for every case separately by experience.

The apparatus according to the invention ensures effective separation of different materials and widens the possibilities offered by the overpressured thin-layer chromatography.

From the above description it should be understood that in the apparatus arrangements of the heating unit, carrier plates and sorbent layers equivalent to those given above and temperature control units for programmed regulation of different with circuit arrangement similar to that shown above can be used and the apparata of such construction will be within the scope of claimed invention; such apparata will depend on the given circumstances and the composition of mixtures to be separated.

What we claim is:

1. A chromatographic apparatus for overpressured thin-layer chromatography, comprising at least one carrier plate arranged adjacent a closed space, a sorbent layer arranged on the surface of said carrier plate, means for transmitting overpressure to the surface of said sorbent layer, a first inlet for forwarding solvent to said sorbent layer for separating in a first direction a composition of unidentified constituents into an array, a second inlet for admitting overpressurizing medium into said closed space, a heating unit for altering the temperature of said sorbent layer and a temperature control unit for energizing said heating unit according to a predetermined time and/or space function.

2. A chromatographic apparatus according to claim 1, wherein said heating unit includes a plate-shaped heating element arranged parallel to said sorbent layer and adjacent said carrier plate.

3. A chromatographic apparatus according to claim 1, comprising a heat insulation element arranged adjacent said carrier plate for blocking heat flow from said heating unit.

4. A chromatographic apparatus according to claim 1, wherein said heating unit comprises at least two plate-shaped heating elements and a carrier plate therebetween in parallel arrangement.

5. A chromatographic apparatus according to claim 1, comprising at least two carrier plates and a heating element therebetween, said heating element forming a part of said heating unit.

6. A chromatographic apparatus according to claim 1, comprising in parallel arrangement at least two heating elements forming a part of said heating unit and at least two carrier plates.

7. A chromatographic apparatus according to claim 1, comprising a metallic carrier plate cooperating with an induction heating unit for heating said sorbent layer.

8. A chromatographic apparatus according to claim 1, further comprising a third inlet for forwarding solvent to said sorbent layer for separating said constituents into an array of subconstituents in a second direction transverse to said first direction.

9. A chromatographic apparatus according to claim 1, wherein said temperature control unit comprises means for sensing the temperature of said sorbent layer and means for controlling said heating unit such that the temperature of said sorbent layer has predetermined stable values during predetermined time periods and predetermined gradients during other predetermined time periods.

10. A chromatographic apparatus for overpressured thin-layer chromatography, comprising at least one carrier plate arranged adjacent a closed space, a sorbent layer arranged on the surface of said carrier plate, means for transmitting overpressure to the surface of said sorbent layer, a first inlet for forwarding solvent to said sorbent layer for separating in a first direction a composition of unidentified constituents into an array, a second inlet for admitting overpressurizing medium into said closed space, a heating unit for altering the temperature of said sorbent layer and a temperature control unit for energizing said heating unit according to a predetermined time and/or space function, wherein said temperature control unit includes a central microprocessor unit connected by its respective inputs and outputs to said heating unit divided into parts for altering the temperature of said sorbent layer in accordance with programmed space and time sequences.

11. A chromatographic apparatus according to claim 10, wherein said temperature control unit includes at least one temperature sensor for detecting the temperature of said sorbent layer, connected via a differential amplifier to a first input of a comparison amplifier, the output of said comparison amplifier being connected to a first input of a first comparator, wherein a second input of said comparison amplifier is connected to an output of a series connection including said central microprocessor unit, a control keyboard or other input means for programming said central microprocessor unit and an integrator, said comparison amplifier forwarding signals of high positive level if signal $U_a$ on its first input is of higher level than the signal $U_b$ on its second output, signals of low positive level if signal $U_a$ on its first input is of approximately the same level as the signal $U_b$ on its second input and signals of negative level if the signal $U_a$ on its first input is of lower level than the signal $U_b$ on its second input, wherein a second input of said first comparator is connected by way of a level shifting unit to an output of a relaxation oscillator, and wherein the output of said first comparator is coupled with a power switch, the output of said power switch forming a control ouput of the temperature control unit.

12. A chromatographic apparatus according to claim 11, wherein said power switch is connected by its input to a relay, said relay being connected via a first input to a second comparator with hysteresis coupled with said first input of said comparison amplifier, and via a second input to a high power supply unit.

13. A chromatographic apparatus according to claim 11, wherein said series connection comprises an optical switch between said central microprocessor unit and said integrator.

14. A chromatographic apparatus for overpressured thin-layer chromatography, comprising at least one carrier plate arranged adjacent a closed space, at least one sorbent layer arranged on the surface of said carrier plate, means for transmitting overpressure generated in said closed space to the surface of said at least one sorbent layer, a first inlet for forwarding solvent to each of said sorbent layers for separating in a first direction samples including unidentified constituents into an array, a second inlet for admitting overpressurizing medium into said closed space, heating elements arranged in close relationship to said carrier plates and a temperature control unit for energizing said heating elements according to a predetermined time and/or space function, wherein said temperature control unit includes a central microprocessor unit connected by respective inputs and outputs to said heating elements divided into parts for altering the temperature of said sorbent layer in space and time sequence determined by a program stored in said central microprocessor unit.

15. A chromatographic apparatus according to claim 14, further comprising a third inlet for forwarding solvent to said sorbent layer for separating said constituents into an array of subconstituents in a second direction transverse to said first direction.

16. A chromatographic apparatus according to claim 14, wherein said temperature control unit includes at least one temperature sensor for detecting the temperature of said sorbent layer, connected via a differential amplifier to a first input of a comparison amplifier, the output of said comparison amplifier being connected to a first input of a first comparator, wherein a second input of said comparison amplifier is connected to an output of a series connection including said central microprocessor unit, a control keyboard or other input means for programming said central microprocessor unit and an integrator, said comparison amplifier forwarding signals of high positive level if signal $U_a$ on its first input is of higher level than the signal $U_b$ on its second output, signals of low positive level if signal $U_a$ on its first input is of approximately the same level as the signal $U_b$ on its second input and signals of negative level if signal $U_a$ on its first input is of lower level than the signal $U_b$ on its second input, wherein a second input of said first comparator is connected by way of a level shifting unit to an output of a relaxation oscillator, and wherein the output of said first comparator is coupled with a power switch, the output of said power switch forming a control output of the temperature control unit.

17. A chromatographic apparatus according to claim 14, wherein said power switch is connected by its input to a relay, said relay being connected via a first input to a second comparator with hysteresis coupled with said first input of said comparison amplifier, and via a second input to a high power supply unit.

18. A chromatographic apparatus according to claim 16, wherein said series connection comprises an optical switch between said central microprocessor unit and said integrator.

19. A chromatographic apparatus according to claim 8, further comprising detector means arranged in predetermined positions with respect to said sorbent layer for detecting constituents or sub-constituents passing fixed positions in said arrays.

20. A chromatographic apparatus according to claim 15 further comprising detector means arranged in predetermined positions with respect to said sorbent layer for detecting constituents or subconstituents passing fixed positions in said arrays.

* * * * *